United States Patent
Hung et al.

(10) Patent No.: US 10,276,801 B2
(45) Date of Patent: Apr. 30, 2019

(54) TRIAZINE-BASED COMPOUND AND LIGHT EMITTING DEVICE

(71) Applicant: Industrial Technology Research Institute, Hsinchu (TW)

(72) Inventors: Wen-Yi Hung, New Taipei (TW); Ken-Tsung Wong, New Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 176 days.

(21) Appl. No.: 15/414,638

(22) Filed: Jan. 25, 2017

(65) Prior Publication Data

US 2018/0212155 A1    Jul. 26, 2018

(51) Int. Cl.
*H01L 51/50*    (2006.01)
*H01L 51/00*    (2006.01)
(Continued)

(52) U.S. Cl.
CPC ........ *H01L 51/0067* (2013.01); *C07D 251/24* (2013.01); *C09K 11/06* (2013.01); *H01L 51/0054* (2013.01); *H01L 51/0059* (2013.01); *H01L 51/0065* (2013.01); *H01L 51/5004* (2013.01); *C09K 2211/1007* (2013.01);
(Continued)

(58) Field of Classification Search
None
See application file for complete search history.

(56) References Cited

U.S. PATENT DOCUMENTS

2003/0170491 A1*  9/2003  Liao .................... H01L 51/5036
                                                          428/690
2016/0164020 A1     6/2016  Kim et al.

FOREIGN PATENT DOCUMENTS

CN    103579530     2/2014
TW    I553934      10/2016

OTHER PUBLICATIONS

Hung et al., Balance the Carrier Mobility to Achieve High Performance Exciplex OLED Using a Triazine-Based Acceptor, 2016, ACS Appl. Mat. Interfaces,. 8, 4811-4818 (Year: 2016).*

(Continued)

*Primary Examiner* — Gregory D Clark
(74) *Attorney, Agent, or Firm* — JCIPRNET

(57) ABSTRACT

Provided is a triazine-based compound represented by following formula (I).

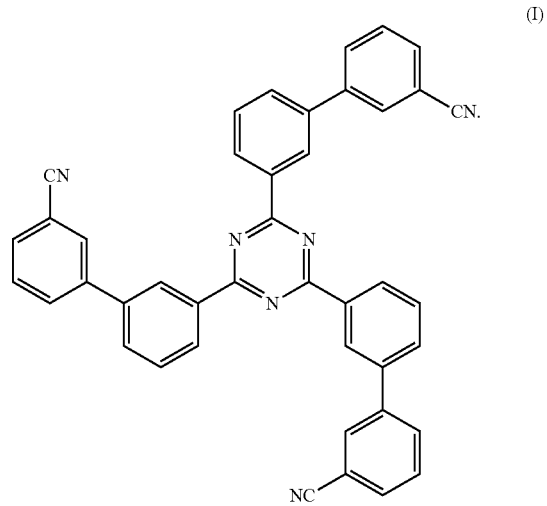

(I)

18 Claims, 11 Drawing Sheets

(51) Int. Cl.
*C07D 251/24* (2006.01)
*C09K 11/06* (2006.01)
*H01L 51/52* (2006.01)

(52) U.S. Cl.
CPC .......... *C09K 2211/1011* (2013.01); *C09K 2211/1029* (2013.01); *C09K 2211/1059* (2013.01); *C09K 2211/1088* (2013.01); *C09K 2211/185* (2013.01); *H01L 51/0072* (2013.01); *H01L 51/0085* (2013.01); *H01L 51/0088* (2013.01); *H01L 51/5012* (2013.01); *H01L 51/5016* (2013.01); *H01L 51/5024* (2013.01); *H01L 51/5044* (2013.01); *H01L 51/5072* (2013.01); *H01L 51/5076* (2013.01); *H01L 51/5278* (2013.01); *H01L 2251/5384* (2013.01); *H01L 2251/552* (2013.01)

(56) References Cited

OTHER PUBLICATIONS

Vaeth and Tang, Light-emitting diodes based on phosphorescent guest/polymeric host systems, 2002, Journal of Applied Physics, vol. 92, No. 7, (Yesr 2002).*
Wen-Yi Hung et al., "Balance the Carrier Mobility to Achieve High Performance Exciplex OLED Using a Triazine-Based Acceptor", ACS Appl. Mater. Interfaces 2016, Feb. 2016, 4811-4818.
K. Goushi et al., "Organic light-emitting diodes employing efficient reverse intersystem crossing for triplet-to-singlet state conversion", JNature Photon. 6, Mar. 2012, 253-258.
H. Nakanotani et al., "Long-range coupling of electron-hole pairs in spatially separated organic donor-acceptor layers", Science Advances, 2, Feb. 2016, 1-7.

* cited by examiner

TRIAZINE-BASED COMPOUND AND LIGHT EMITTING DEVICE

TECHNICAL FIELD

The disclosure relates to a triazine-based compound and a light emitting device.

BACKGROUND

Organic light emitting diodes (OLED) devices are becoming an increasingly important category of thin film organic semiconductor devices. Generally speaking, an OLED device includes an anode, an organic light emitting layer, and a cathode, wherein the organic light emitting layer includes a host material and a guest material. An OLED device operates by applying an external electric field, wherein electrons enter from the cathode and holes enter from the anode, of the OLED device. When the electrons and the holes meet after they travel through the electron transport layer and the hole transport layer, respectively, energy will be generated in the form of light (luminescence). This is a short-hand description of the organic light emitting phenomenon.

The OLED device, having characteristics such as free viewing angle, simple fabrication process, low production cost, fast response, wide operation temperature range, and full color display, etc., is expected to become the mainstream of new flat-panel displays.

SUMMARY

One of the present embodiments comprises a triazine-based compound. The compound is represented by formula (I).

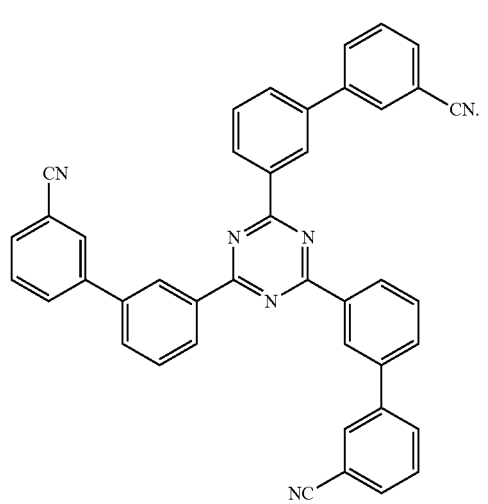

(I)

Another of the present embodiments comprises a light emitting device. The light emitting device includes a cathode, an anode, an organic light emitting layer between the anode and the cathode, a hole transport layer between the organic light emitting layer and the anode, and an electron transport layer between the organic light emitting layer and the cathode, wherein the electron transport layer comprises the triazine-based compound represented by above formula (I).

Yet another of the present embodiments comprises a light emitting device. The light emitting device includes a cathode, an anode, a hole transport layer between the cathode and the anode, and an organic layer between the cathode and the hole transport layer. The organic layer includes an organic compound and the triazine-based compound represented by above formula (I). A combination of the triazine-based compound and the organic compound forms an exciplex, wherein a difference between a lowest unoccupied molecular orbital (LUMO) level of the triazine-based compound and a highest occupied molecular orbital (HOMO) level of the organic compound is 2.92 eV or less.

Yet another of the present embodiments comprises a light emitting device. The light emitting device includes a cathode, an anode, two light-emitting elements between the cathode and the anode, and a charge generation layer (CGL) disposed between the two light-emitting elements. Each of the light-emitting elements includes the triazine-based compound represented by above formula (I) and an organic compound with a red dopant. A combination of the triazine-based compound and the organic compound forms an exciplex for being a co-host, wherein a difference between a LUMO level of the triazine-based compound and a HOMO level of the organic compound is 2.92 eV or less, the dopant has a singlet energy lower than that of the exciplex, and the dopant has a triplet energy lower than that of the exciplex.

Yet another of the present embodiments comprises a light emitting device. The light emitting device includes a cathode, an anode, a green-light emitting element, a blue-light emitting element, a red-light emitting element, and charge generation layers (CGL) disposed between two of above light-emitting elements. The green-light, blue-light and red-light emitting elements are disposed between the anode and the cathode. The green-light emitting element comprises the triazine-based compound represented by above formula (I) and an organic compound, and the red-light emitting element comprises the triazine-based compound represented by above formula (I) and the organic compound with a red dopant. A combination of the triazine-based compound and the organic compound forms an exciplex, wherein a difference between a LUMO level of the triazine-based compound and a HOMO level of the organic compound is 2.92 eV or less, the red dopant has a singlet energy lower than that of the exciplex, and the red dopant has a triplet energy lower than that of the exciplex.

Several exemplary embodiments accompanied with figures are described in detail below to further describe the disclosure in details.

DESCRIPTION OF THE EMBODIMENTS

Figure 1:
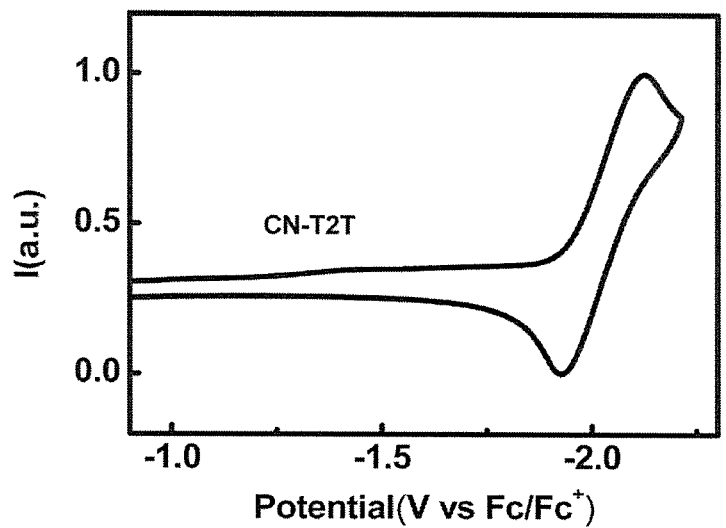
FIG. 1 is a curve illustrating one quasi-reversible reduction potential of the triazine-based compound of the disclosure.

Reference will now be made in detail to the present preferred embodiments of the disclosure, examples of which are illustrated in the accompanying drawings. Nevertheless, the disclosure may be embodied in many different forms and should not be construed as limited to the embodiments set forth herein. In the drawings, for the purpose of clarity and specificity, the sizes and the relative sizes of each layer and region may not be illustrated in accurate proportion. Wherever possible, the same reference numbers are used in the drawings and the description to refer to the same or like parts.

The triazine-based compound according to the disclosure is a compound represented by formula (I). The triazine-based compound of formula (I) is named as 3',3''',3'''''-(1,3,5-triazine-2,4,6-triyl)tris(([1,1'-biphenyl]-3-carbonitrile)) (hereinafter abbreviated as "CN-T2T").

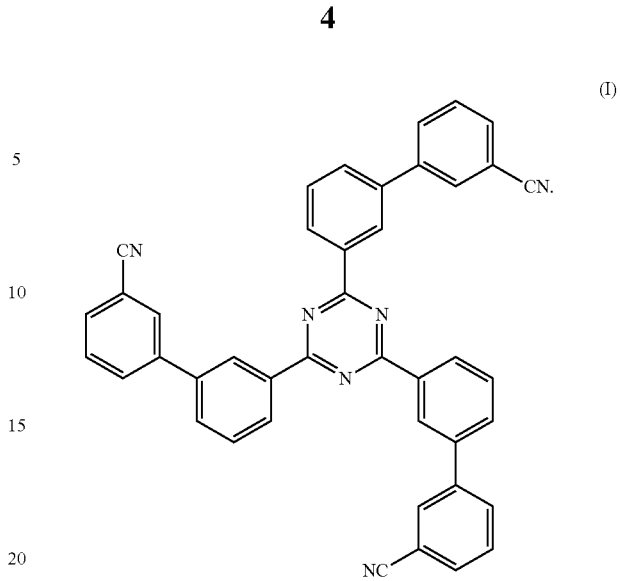

CN-T2T may be synthesized in two steps with a high yield from a triazine tribromo compound (1), which was first transformed into triboronic ester (2) and subsequently reacted with readily available 3-bromobenzonitrile under Suzuki coupling condition (Please refer to Scheme 1).

Scheme 1

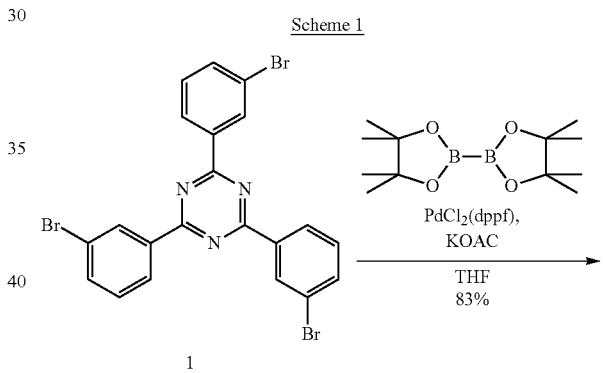

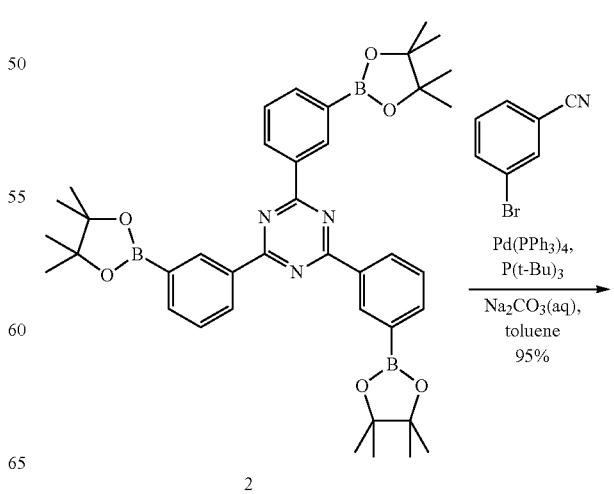

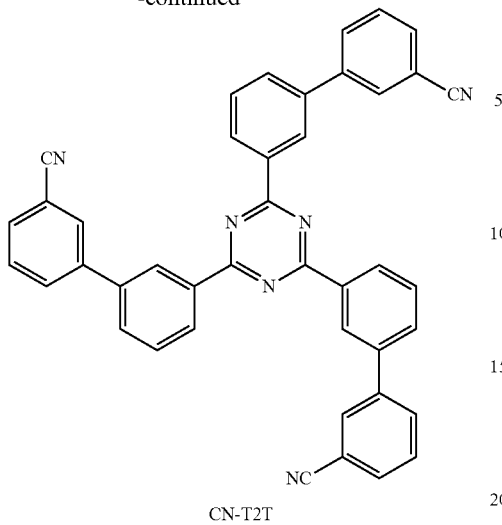

CN-T2T

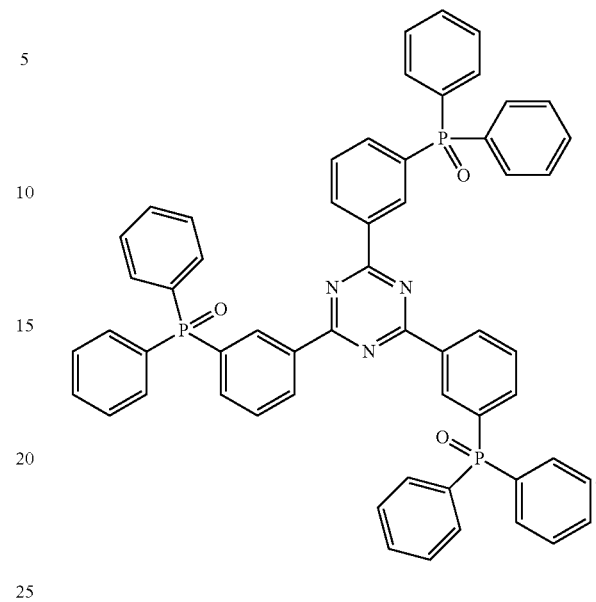

(II)

CN-T2T exhibits excellent thermal stability with a high decomposition temperature ($T_d$) of 418° C. (refer to 5% weight loss) measured by thermogravimetric analysis (TGA). No evident glass transition temperature but a melting temperature was observed at 286 ° C. for CN-T2T by differential scanning calorimetry (DSC) analysis. In addition, one quasi-reversible reduction potential (−2.02 V vs Fc/Fc$^+$) of CN-T2T was detected by cyclic voltammetry analysis, and the result is shown in FIG. 1. This result was used to calculate the lowest unoccupied molecular orbital (LUMO) level to be −2.78 eV as referred to the redox couple of ferrocene, and the highest occupied molecular orbital (HOMO) level was estimated by subtracting the energy gap from the LUMO level, and thus the HOMO level is −6.70 eV.

Figure 2:
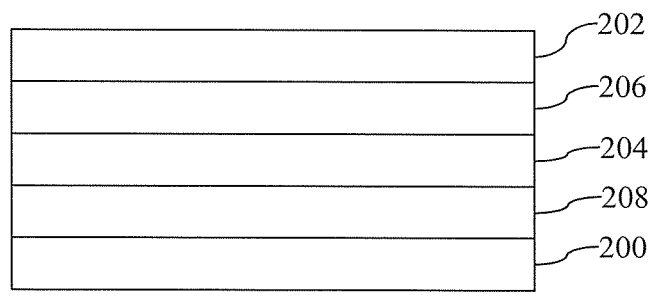
FIG. 2 is a schematic, cross-sectional diagram of a light emitting device in accordance with a first exemplary embodiment of the disclosure.

FIG. 2 is a schematic, cross-sectional diagram of a light emitting device in accordance with a first exemplary embodiment of the disclosure.

Referring to FIG. 2, a light emitting device includes a cathode 200, an anode 202, an organic light emitting layer 204 disposed between the anode 202 and the cathode 200, a hole transport layer 206 disposed between the organic light emitting layer 204 and the anode 202, and an electron transport layer 208 disposed between the organic light emitting layer 204 and the cathode 200, wherein the electron transport layer 208 comprises the triazine-based compound represented by above formula (I) (i.e. CN-T2T). The electron transport layer 208 is not limited to a single layer, and two or more layers made of another compound may be stacked. For example, the electron transport layer 208 may further includes another triazine-based compound represented by formula (II).

In the first exemplary embodiment, the cathode 200 may be any suitable material or combination of materials known in the art, such that the cathode 200 is capable of conducting electrons and injecting them into the electron transport layer 208. The cathode 200 may be transparent or opaque, and may be reflective. Metals and metal oxides are examples of the material of the cathode 200. In addition, the cathode 200 may be a single layer, or may have a compound structure.

In the first exemplary embodiment, the anode 202 may be any suitable anode that is sufficiently conductive to transport holes to the hole transport layer 206. The material of the anode 202 preferably has a work function such as 4.8-5.1 eV. For example, the material of the anode 202 include conductive metal oxides, such as indium tin oxide (ITO), indium zinc oxide (IZO), aluminium zinc oxide (AZO), or metals.

In the first exemplary embodiment, the hole transport layer 206 may include a material capable of transporting holes. The hole transport layer 206 may be intrinsic (undoped), or doped. Doping may be used to enhance conductivity. The organic light emitting layer 204 may include an organic material capable of emitting light when a current is passed between the anode 202 and the cathode 200.

Figure 3:
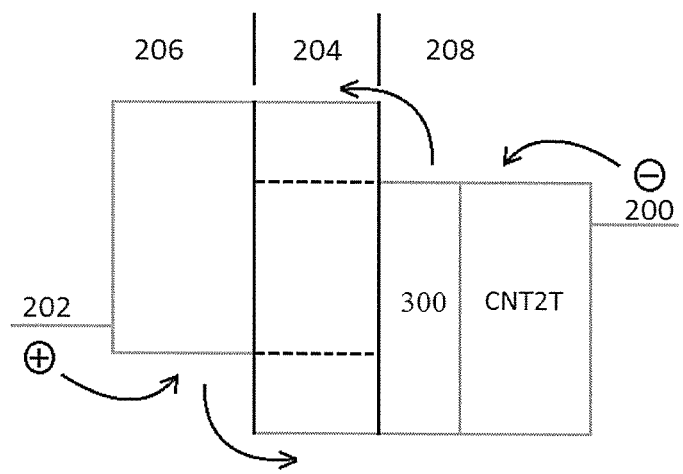
FIG. 3 is a schematic diagram illustrating energy level of the light emitting device illustrated in FIG. 2.

FIG. 3 is a schematic diagram illustrating energy level of the light emitting device in FIG. 2.

In FIG. 3, holes are injected from the anode 202 into the organic light emitting layer 204, and electron are injected from the cathode 200 into the organic light emitting layer 204. The material of the electron transport layer 208 with a high electron-transporting property, and thus it may improve the external quantum efficiency (EQE) of the light emitting device.

In one example of the first exemplary embodiment, the cathode 200 is Liq/Al, the anode 202 is ITO, the organic light emitting layer 204 includes the triazine-based compound represented by above formula (II) and a donor material, the hole transport layer 206 is a stack of 9,9'-(1,3-phenylene)bis-9H-carbazole (mCP) and mCP:4%ReO$_3$, and the electron transport layer 208 is a stack of the triazine-based compound 300 represented by above formula (II) and CN-T2T. The donor material in the organic light emitting layer 204 may be at least one compound selected from following formulas (III) and (IV).

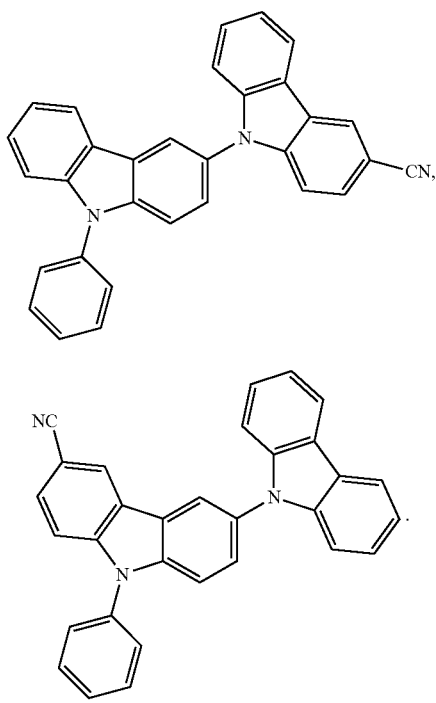

Figure 4:
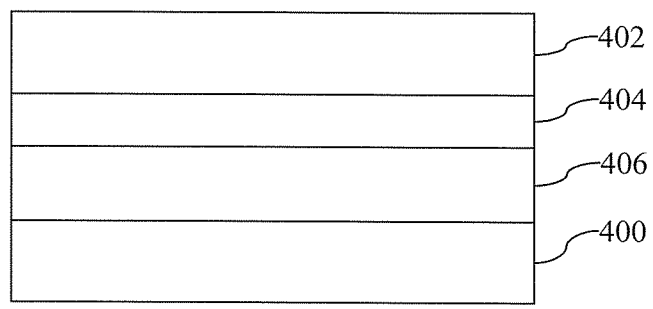
FIG. 4 is a schematic, cross-sectional diagram of a light emitting device in accordance with a second exemplary embodiment of the disclosure.

FIG. 4 is a schematic, cross-sectional diagram of a light emitting device in accordance with a second exemplary embodiment of the disclosure.

Referring to FIG. 4, a light emitting device includes a cathode 400, an anode 402, a hole transport layer 404 disposed between the cathode 400 and the anode 402, and an organic layer 406 between the cathode 400 and the hole transport layer 404. The organic layer 406 includes an organic compound as a donor and the triazine-based compound represented by above formula (I) (i.e. CN-T2T) as an acceptor. The cathode 400 and the anode 402 may refer to the description in regard to the first exemplary embodiment and will no longer repeated.

Figure 5:
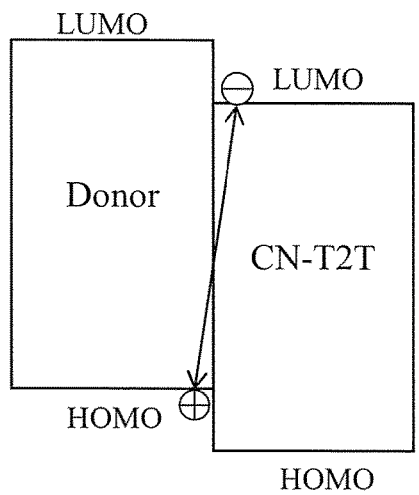
FIG. 5 is a schematic diagram illustrating energy level of the light emitting device illustrated in FIG. 4.

FIG. 5 is a schematic diagram illustrating energy level of the light emitting device in FIG. 4.

In FIG. 5, a difference between a LUMO level of CN-T2T and a HOMO level of the organic compound (i.e. Donor); for example, the difference is 2.92 eV or less, and thus a combination of CN-T2T and the organic compound can form an exciplex as an emitter. In one embodiment, an energy level offset between the HOMO levels of CN-T2T and the organic compound 500 is more than 0.4 eV, and an energy level offset between the LUMO levels of CN-T2T and the organic compound 500 is more than 0.4 eV. Also, the large energy level offset is beneficial for carriers' accumulation at the interface of the organic compound 500 and CN-T2T. In the second exemplary embodiment, the organic compound 500 has a hole-transport property and CN-T2T has an electron-transport property, and thus the electron-hole capture in the organic layer 406 is efficient without additional carrier injection barrier from donor (or acceptor) molecule. In one embodiment, carriers mobilities are balanced in the organic layer 406, leads to a highly efficient exciplex OLED with external quantum efficiency (EQE). Since the organic compound 500 has a hole-transport property, it may be contained in the hole transport layer 404, and the hole transport layer 404 may be doped with dopants for enhancing conductivity.

Referring to FIG. 4 again, the organic compound in the organic layer 406 includes, for example, carbazole derivative (Tris-PCz), 4,4',4"-tri(N-carbazolyl) triphenylamine (TCTA) or di[4-(N,N-ditolyl-amino)-phenyl]cyclohexane (TAPC). In one embodiment, the organic layer 406 exhibits green light or yellow light.

Moreover, the organic layer 406 may be doped with a dopant, and the exciplex is used as a co-host. The dopant may have a singlet energy lower than that of the exciplex, and the dopant may have a triplet energy lower than that of the exciplex. The dopant may include a fluorescent dopant or a phosphorescent dopant. The fluorescent dopant for yellow light and the fluorescent dopant for red light are hereinbelow referred to as "yellow fluorescent dopant" and "red fluorescent dopant," respectively. The phosphorescent dopant for yellow light and the phosphorescent dopant for red light are hereinbelow referred to as "yellow phosphorescent dopant" and "red phosphorescent dopant," respectively. Therefore, by doping few (fluorescent or phosphorescent) dopant in the organic layer 106, the light emitting device may attain high EQE values in yellow or red. The content of the dopant in the organic layer 406 is, for example, 5 wt % or less. In one embodiment, the content of the dopant in the organic layer 406 is 1 wt % or less.

Figure 6:
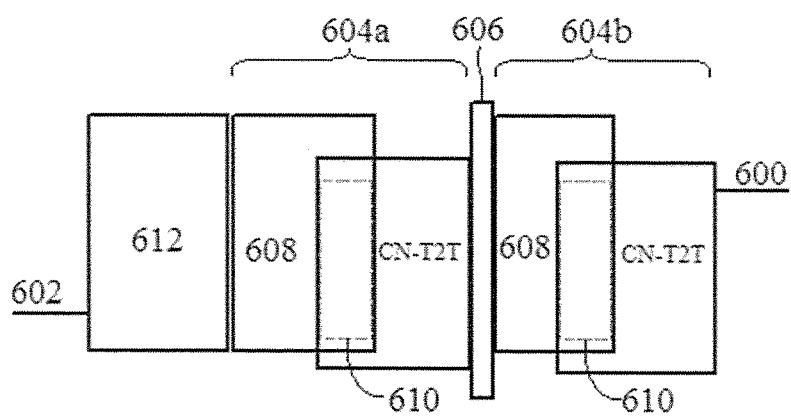
FIG. 6 is a schematic diagram illustrating energy level of a light emitting device in accordance with a third exemplary embodiment of the disclosure.
Figure 7:
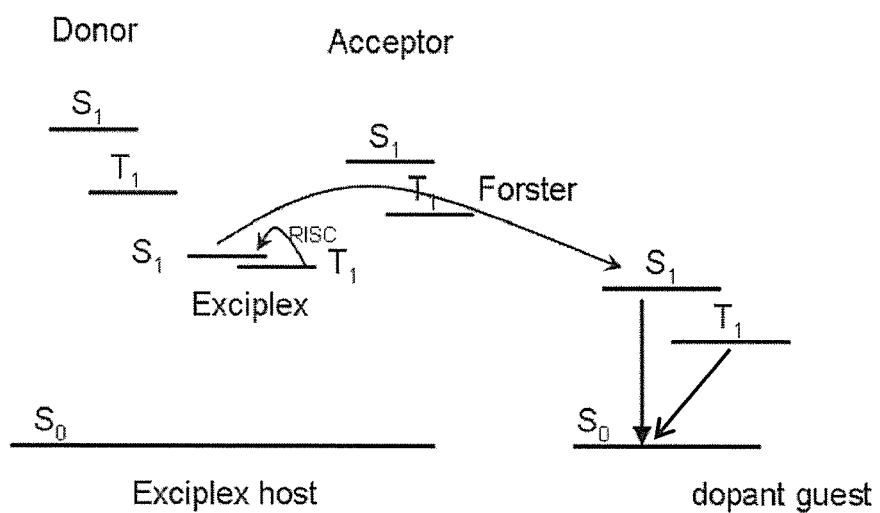
FIG. 7 is a schematic diagram illustrating energy level of the light-emitting element in FIG. 6.

FIG. 6 is a schematic diagram illustrating energy level of a light emitting device in accordance with a third exemplary embodiment of the disclosure. FIG. 7 is a schematic diagram illustrating energy level of the light-emitting element in FIG. 6.

Referring to FIG. 6, a light emitting device includes a cathode 600, an anode 602, two light-emitting elements 604a and 604b between the anode 602 and the cathode 600, and a charge generation layer (CGL) 606 between the two light-emitting elements 604a and 604b. Each of the light-emitting elements 604a and 604b comprises CN-T2T and an organic compound 608 with a red dopant, wherein the red dopant includes a red fluorescent dopant or a red phosphorescent dopant. The organic compound 608 includes, for example, Tris-PCz, TCTA or TAPC; preferably, TAPC. A combination of CN-T2T and the organic compound 608 forms an exciplex 610 as a co-host, wherein a difference between a LUMO level of CN-T2T and a HOMO level of the organic compound 608 is 2.92 eV or less, the red dopant has a singlet energy lower than that of the exciplex 610, and the red dopant has a triplet energy lower than that of the exciplex 610. In one embodiment, the red dopant includes a red fluorescent dopant or a red phosphorescent dopant. The content of the red dopant in the light-emitting elements 604a and 604b is, for example, 5 wt % or less. In one embodiment, the content of the red dopant in the light-emitting elements 604a and 604b is 1 wt % or less. Moreover, the cathode 600 and the anode 602 may refer to the description in regard to the first exemplary embodiment and will no longer repeated. Moreover, a hole transport layer 612 may be disposed between the anode 602 and the light-emitting elements 604a, and it may be the same as the organic compound 608 with few metal oxide to enhance the conductivity.

In FIG. 7, the donor is the organic compound (608 in FIG. 6), the acceptor is CN-T2T, and the exciplex (610 in FIG. 6) is co-host. Thus, energy can effectively transfer from the exciplex to the dopant (i.e. red dopant).

Figure 8:
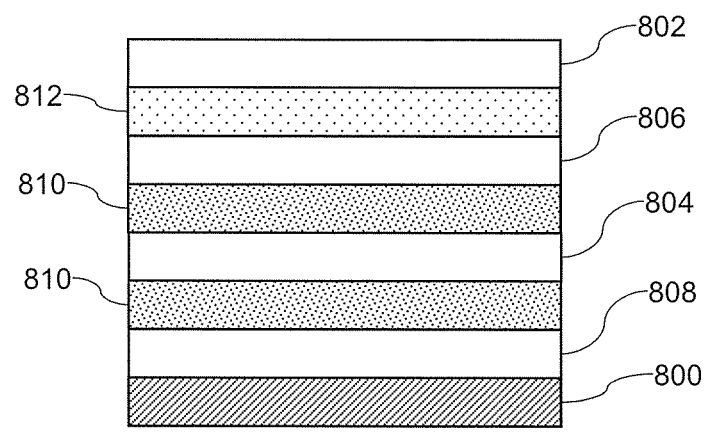
FIG. 8 is a schematic, cross-sectional diagram of a light emitting device in accordance with a fourth exemplary embodiment of the disclosure.

FIG. 8 is a schematic, cross-sectional diagram of a light emitting device in accordance with a fourth exemplary embodiment of the disclosure.

Referring to FIG. 8, a light emitting device includes a cathode 800 and an anode 802. In the light emitting device, a green-light emitting element 804, a blue-light emitting element 806, and a red-light emitting element 808 are disposed between the anode 802 and the cathode 800, and a charge generation layer (CGL) 810 is between two of those light-emitting elements 804, 806 and 808. The green-light emitting element 804 comprises CN-T2T and an organic compound, and the red-light emitting element 808 comprises CN-T2T and the organic compound with a red dopant, wherein the red dopant includes a red fluorescent dopant or a red phosphorescent dopant, for instance. In the light-emitting element 804, a combination of CN-T2T and the organic compound forms an exciplex for emitting green light. In the light-emitting element 806, the exciplex is formed as a co-host and then energy is transferred to the red dopant for emitting red light. A difference between a LUMO level of CN-T2T and a HOMO level of the organic compound is 2.92 eV or less, the red dopant has a singlet energy lower than that of the exciplex, and the red dopant has a triplet energy lower than that of the exciplex. Accordingly, the organic compound includes, for example, Tris-PCz, TCTA or TAPC.

In fourth exemplary embodiment, the blue-light emitting element 806 may be well-known blue OLED element, such as blue exciplex formed by a combination of a donor and an acceptor. For example, the acceptor may be the triazine-based compound represented by above formula (II), and the donor may be one of the compounds selected from above formulas (III) and (IV). In addition, a hole transport layer 812 may be disposed between the anode 802 and the light-emitting element 806. Moreover, the cathode 800, the anode 802 and the hole transport layer 812 may refer to the description in regard to the first exemplary embodiment and will no longer repeated. In addition, the placements of those light-emitting elements 804, 806 and 808 may be swapped and not limited in the light emitting device of FIG. 8.

In the following, the disclosure will be described more specifically by way of Examples, however, it is to be understood that the disclosure is not limited to the following Examples but can be practiced with appropriate changes.

EXAMPLE 1

A light emitting device is produced that is composed of Tris-PCz and CN-T2T as functional materials. In detail, the light emitting device is: ITO/4% ReO$_3$:Tris-PCz (60 nm)/Tris-PCz (15 nm)/Tris-PCz:CN-T2T(1:1) (25 nm)/CN-T2T (50 nm)/Liq (0.5 nm)/Al (100 nm). Here, ITO is the anode, 8-hydroxyquinolinolatolithium (Liq) and Al are the cathode, 4% ReO$_3$:Tris-PCz is the hole-transporting layer (HTL), and the organic layer consists of Tris-PCz and CN-T2T. The molar ratio of Tris-PCz:CN-T2T in the organic layer is 1:1 to balance the carrier therein, attaining high electron-hole capture probability. ReO$_3$ is used as a dopant material in Tris-PCz to produce ohmic contact for lowering the hole injection barrier from ITO to Tris-PCz.

The HOMO and LUMO levels of Tris-PCz are −5.6 eV and −2.1 eV respectively. The structural formula of Tris-PCz is as follow.

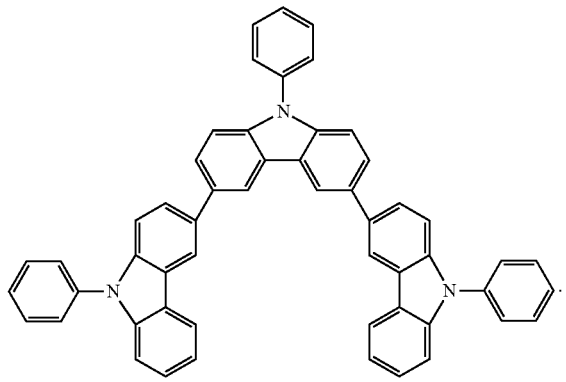 [SMILES: c1ccc(-n2c3ccccc3c3cc(-c4ccc5c(c4)c4cc(-c6ccc7c(c6)c6ccccc6n7-c6ccccc6)ccc4n5-c4ccccc4)ccc32)cc1]

COMPARATIVE EXAMPLE 1

A light emitting device is produced the same as example 1 except for only using Tris-PCz as the organic layer.

COMPARATIVE EXAMPLE 2

A light emitting device is produced the same as example 1 except for only using CN-T2T as the organic layer.

Photophysical Property of Example 1 and Comparative Examples 1-2

Figure 9:
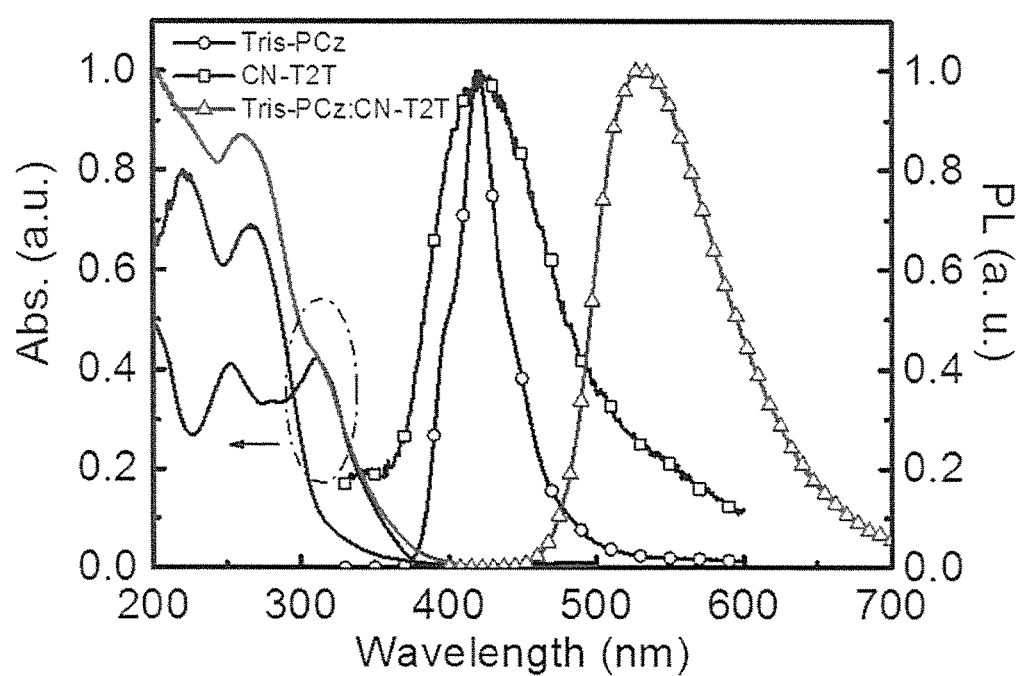
FIG. 9 is a curve diagram illustrating absorption and PL spectra for the light emitting device of Example 1 and Comparative examples 1-2.

FIG. 9 shows abs. and PL spectra for the light emitting device of Example 1 and Comparative examples 1-2. According to FIG. 9, it is clear that Tris-PCz:CN-T2T can form the exciplex. Moreover, the PLQY for Tris-PCz:CN-T2T is up to 53% after measurement.

EXAMPLE 2

A light emitting device is produced the same as example 1 except for replacing Tris-PCz with 4,4',4''-tri(N-carbazolyl)triphenylamine (TCTA). TCTA has similar energy levels (HOMO/LUMO=−5.62/−2.2 eV) to Tris-PCz.

TOF (Time-of-Flight) Mobilities of Examples 1-2

Figure 10A:
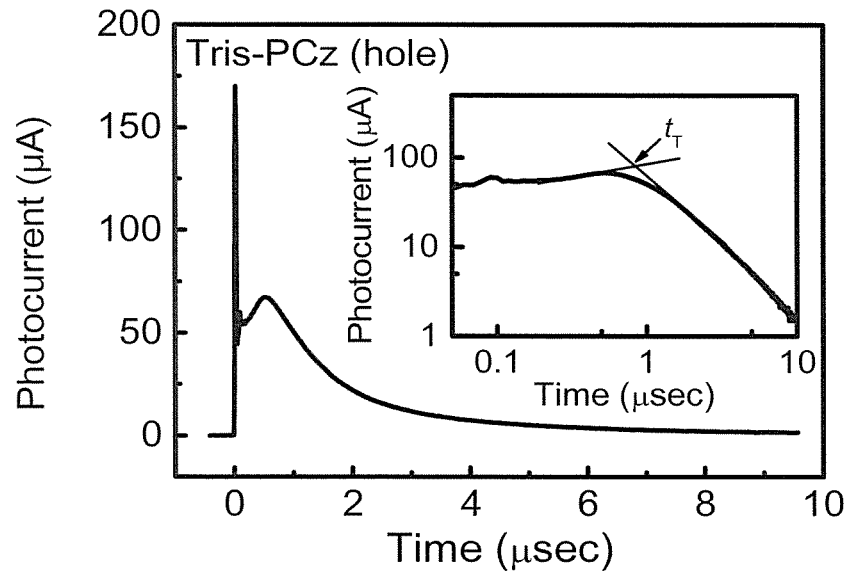
FIG. 10A is a curve diagram illustrating photocurrent along time in accordance with Example 1.
Figure 10B:
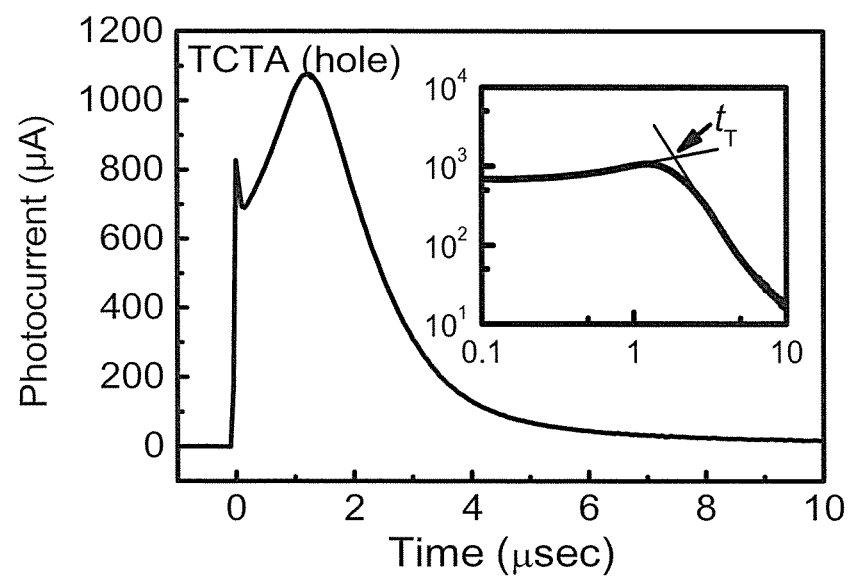
FIG. 10B is a curve diagram illustrating photocurrent along time in accordance with Example 2.

FIG. 10A and FIG. 10B show the photocurrent along time in accordance with Examples 1-2. It can be seen that the photocurrent of example 2 is much higher than that of example 1. According to the results, even though the TCTA has similar energy levels to Tris-PCz, their TOF mobilities have a great gap because the charge mobility between CN-T2T and Tris-PCz are more matched than that between CN-T2T and TCTA.

EXAMPLE 3

A light emitting device is produced the same as example 1 except for doping 1 wt % 5,6,11,12-tetraphenylnaphthacene (Rubrene) as a fluorescent dopant.

EXAMPLE 4

A light emitting device is produced the same as example 1 except for doping 1 wt % 4-(dicyanomethylene)-2-t-butyl-6-(1,1,7,7-tetramethyljulolidyl-9-enyl)-4H-pyran (DCJTB) as a fluorescent dopant.

EL Characteristics of Examples 1-4

Figure 11:
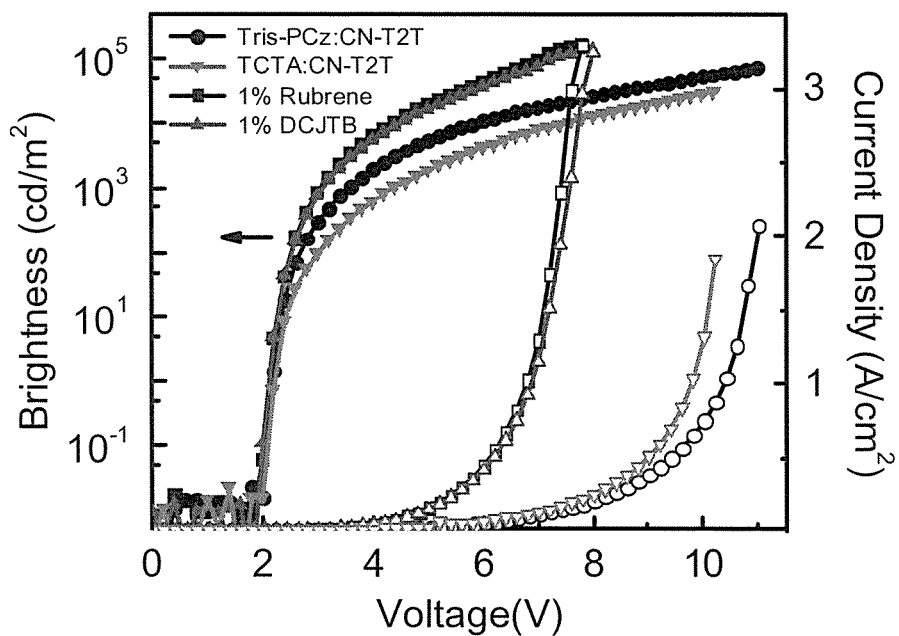
FIG. 11 is a curve diagram illustrating current density-voltage-luminance (J-V-L) characteristics of Examples 1-4.
Figure 12:
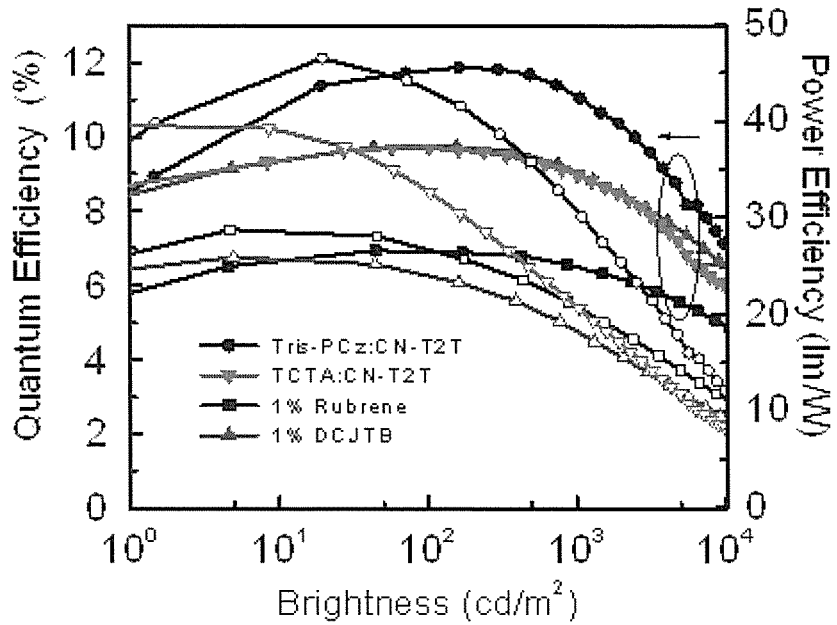
FIG. 12 is a curve diagram illustrating external quantum (EQE) and power efficiencies (PE) as a function of brightness in accordance with Examples 1-4.
Figure 13:
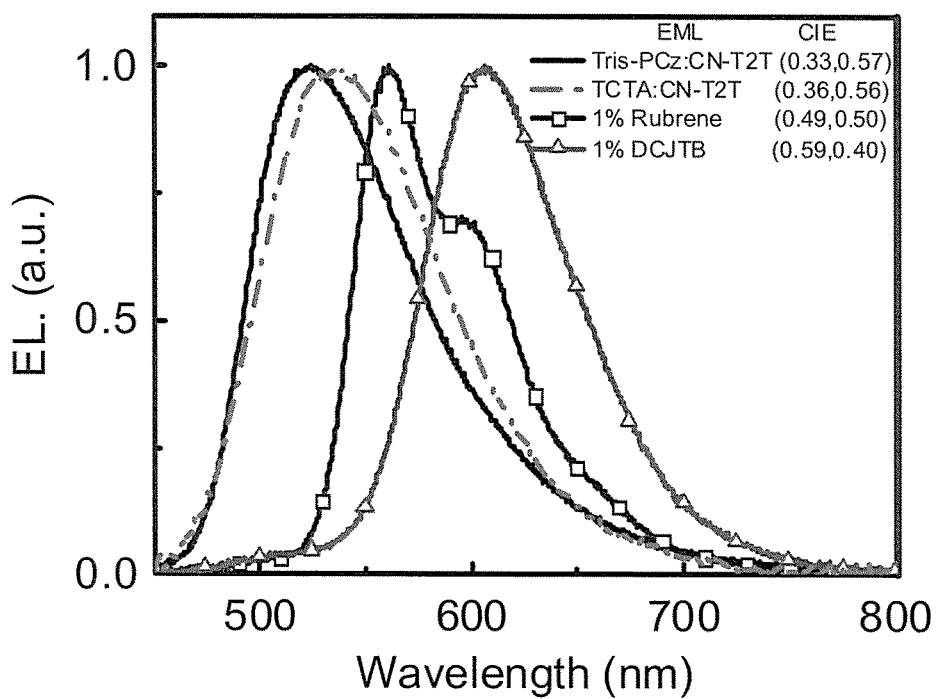
FIG. 13 is an electroluminescence (EL) spectra for the light emitting device of Examples 1-4.

FIG. 11 shows current density-voltage-luminance (J-V-L) characteristics of Examples 1-4. FIG. 12 shows external quantum (EQE) and power efficiencies (PE) as a function of brightness in accordance with Examples 1-4. FIG. 13 shows an EL spectra for the light emitting device of Examples 1-4. The pertinent data are summarized in Table 1.

TABLE 1

| EML | $V_{on}$ [V] | $L_{max}$ [cd/m$^2$] | $I_{max}$ [mA/cm$^2$] | EQE [%] | CE [cd/A] | PE [lm/W] | EQE at 1000 nit [%, V] |
|---|---|---|---|---|---|---|---|
| TrisPCz: CN-T2T | 2.0 | 73800 (11.0 V) | 2070 | 11.9 | 37.0 | 46.5 | 11.1, 3.6 |
| TCTA: CN-T2T | 2.0 | 30400 (10.2 V) | 1850 | 9.7 | 31.1 | 39.6 | 9.0, 4.4 |
| 1 wt % Rubrene | 2.0 | 166000 (7.8 V) | 3300 | 6.9 | 21.4 | 28.1 | 6.6, 3.0 |
| 1 wt % DCJTB | 2.0 | 140500 (8.0 V) | 3250 | 9.7 | 19.3 | 23.3 | 9.1, 3.1 |

As shown in FIGS. 11-13 and Table 1, all devices of examples 1-4 have the maximum external quantum (EQE) more than 5% and up to 11.1% (37.0 cd/A, 46.5 lm/W) at an exceptionally low driving voltage of 2.0 V at 1000 nit.

EXAMPLE 5

A light emitting device is produced that is composed of di-[4-(N,N-ditolyl-amino)-phenyl]cyclohexane (TAPC) and CN-T2T as functional materials. In detail, the light emitting device is: ITO/4% ReO$_3$:TAPC (60 nm)/TAPC (15 nm)/TAPC:CN-T2T (1:1) (20 nm)/CN-T2T (50 nm)/Liq/Al/HATCN (20 nm)/HATCN:TAPC (2:1) (10 nm)/TAPC (40 nm)/TAPC:CN-T2T (1:1) (20 nm)/CN-T2T (50 nm)/Liq/Al. Here, the organic compound in the light emitting elements is di-[4-(N,N-ditolyl-amino)-phenyl]cyclohexan (TAPC), and the molar ratio of TAPC:CN-T2T in the organic layer is 1:1 to balance the carrier therein, attaining high electron-hole capture probability. Liq/Al/dipyrazino[2,3f:2',3'-h]quinoxaline-2,3,6,7,10,11-hexacarbonitrile (HATCN) is CGL. TAPC has similar energy levels (HOMO/LUMO =−5.3 eV/−1.8 eV) to Tris-PCz.

EXAMPLE 6

A light emitting device is produced the same as example 5 except for doping 1 wt % DCJTB.

EXAMPLE 7

A tandem light emitting device is produced the same as example 5 except for doping 1 wt % PER-1-04.

EL Characteristics of Examples 5-7

Figure 14:
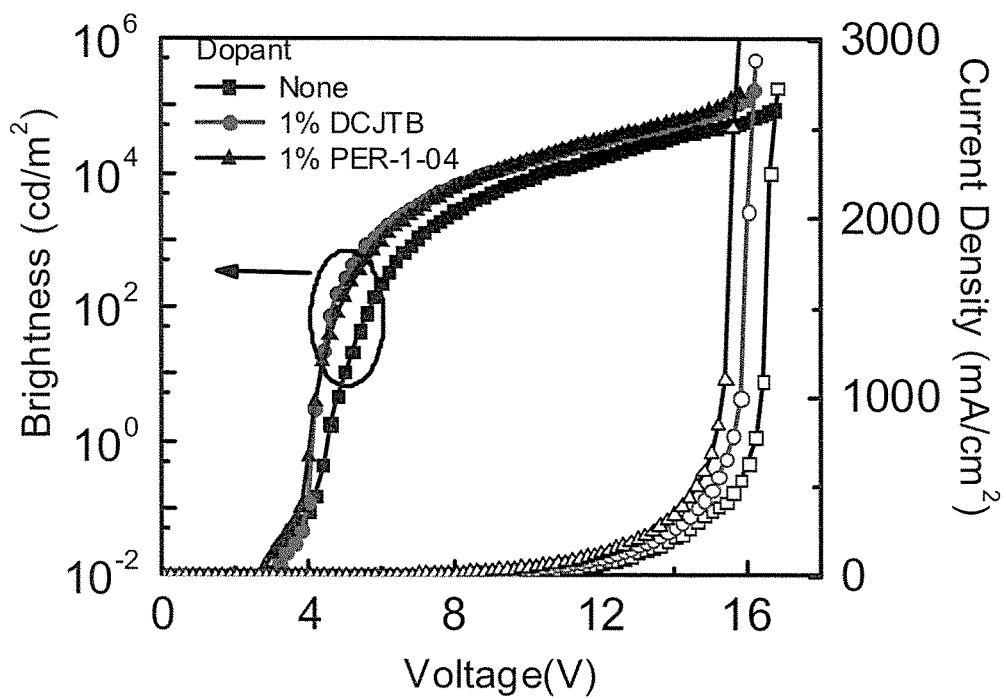
FIG. 14 is a curve diagram illustrating J-V-L characteristics of Examples 5-7.
Figure 15:
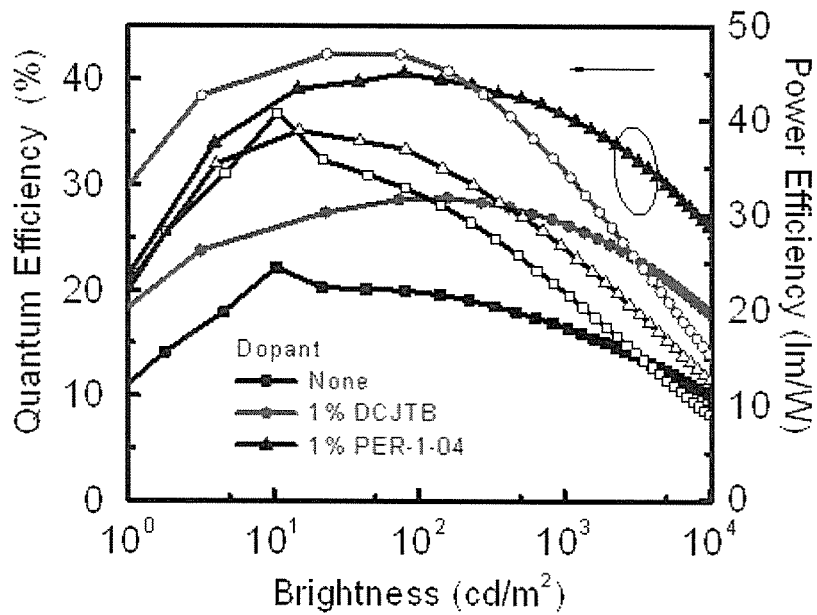
FIG. 15 is a curve diagram illustrating EQE and PE as a function of brightness in accordance with Examples 5-7.
Figure 16:
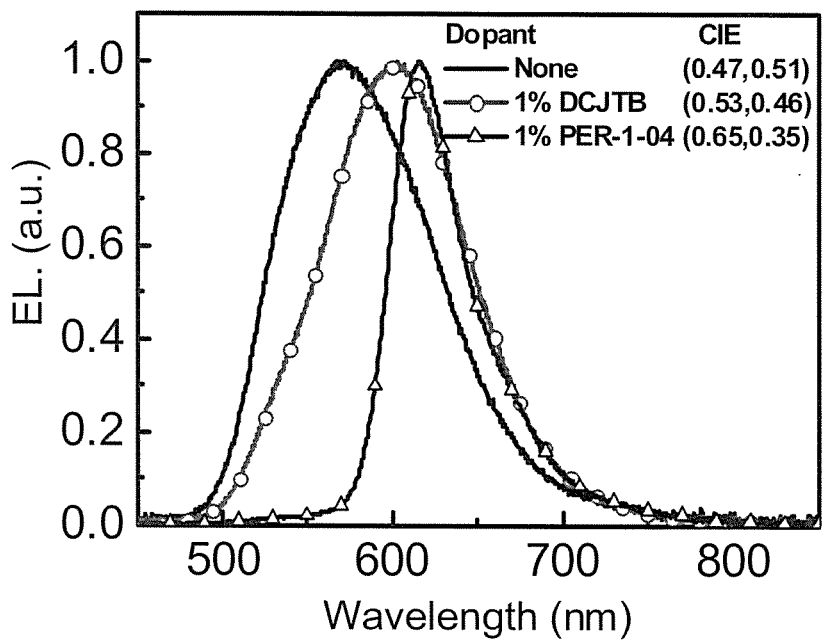
FIG. 16 is an EL spectra for the light emitting device of Examples 5-7.

FIG. 14 shows J-V-L characteristics of Examples 5-7. FIG. 15 shows EQE and PE as a function of brightness in accordance with Examples 5-7. FIG. 16 shows an EL spectra for the light emitting device of Examples 5-7. The pertinent data are summarized in Table 2.

TABLE 2

| Dopant | $V_{on}$ [V] | $L_{max}$ [cd/m$^2$] | $I_{max}$ [mA/cm$^2$] | $h_{ext}$ max [%, cd/A] | $h_p$ max [lm/W] | EQE at 1000 nit [%, V] |
|---|---|---|---|---|---|---|
| None | 4.0 | 87832 (16.8 V) | 2737 | 22.1, 64.8 | 40.7 | 16.4, 7.0 |
| 1 wt % DCJTB | 4.0 | 171562 (16.2 V) | 2916 | 28.7, 68.8 | 46.8 | 26.0, 5.8 |

TABLE 2-continued

| Dopant | $V_{on}$ [V] | $L_{max}$ [cd/m$^2$] | $I_{max}$ [mA/cm$^2$] | $h_{ext}$ max [%, cd/A] | $h_p$ max [lm/W] | EQE at 1000 nit [%, V] |
|---|---|---|---|---|---|---|
| 1 wt % PER-1-04 | 4.0 | 150709 | 3091 | 40.6, 56.5 | 38.9 | 36.8, 6.0 |

As shown in FIGS. 14-16 and Table 2, all devices of examples 5-7 have high EQE up to 36.8% (56.5 cd/A, 38.9 lm/W) at an exceptionally low driving voltage of 4.0 V at 1000 nit.

EXAMPLE 8

A tandem light emitting device is produced the same as example 5 except for doping 1 wt % Mpq as a phosphorescent dopant. The structural formula of Mpq is as follow.

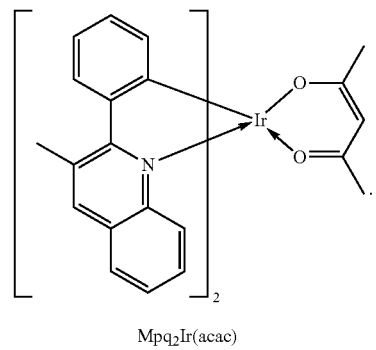

Mpq$_2$Ir(acac)

EXAMPLE 9

A tandem light emitting device is produced the same as example 5 except for doping 1 wt % OS1. The structural formula of OS1 is as follow.

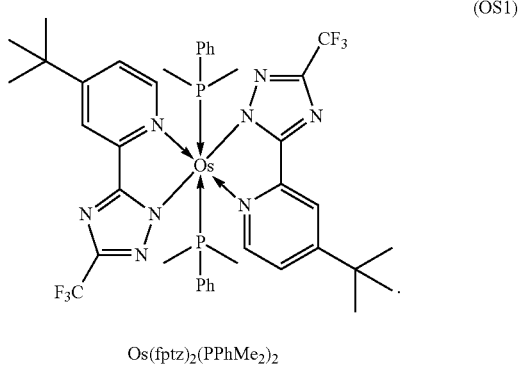

Os(fptz)$_2$(PPhMe$_2$)$_2$

EXAMPLE 10

A tandem light emitting device is produced the same as example 5 except for doping 1 wt % OS2. The structural formula of OS2 is as follow.

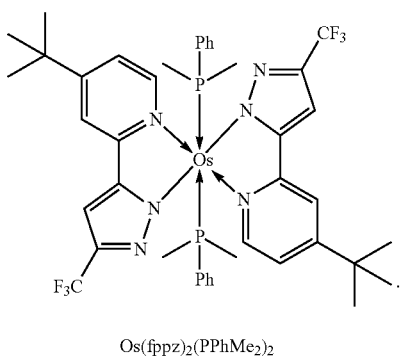

Os(fppz)₂(PPhMe₂)₂
(OS2)

EL characteristics of Examples 8-10

Figure 17:
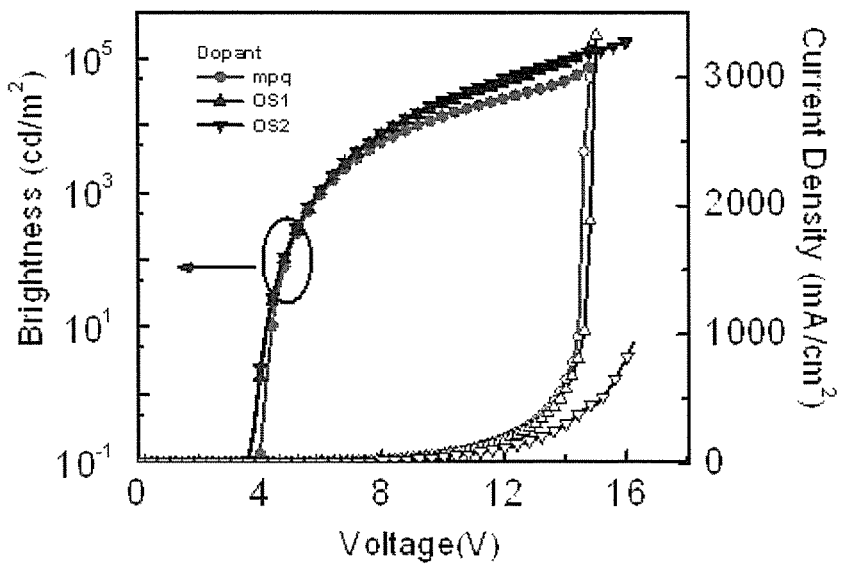
FIG. 17 is a curve diagram illustrating J-V-L characteristics of Examples 8-10.
Figure 18:
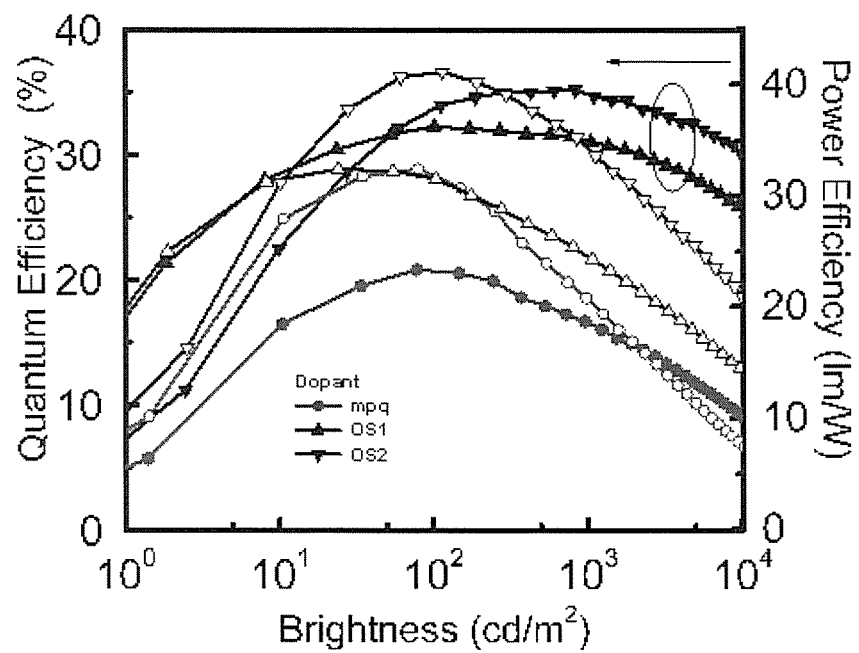
FIG. 18 is a curve diagram illustrating EQE and PE as a function of brightness in accordance with Examples 8-10.
Figure 19:
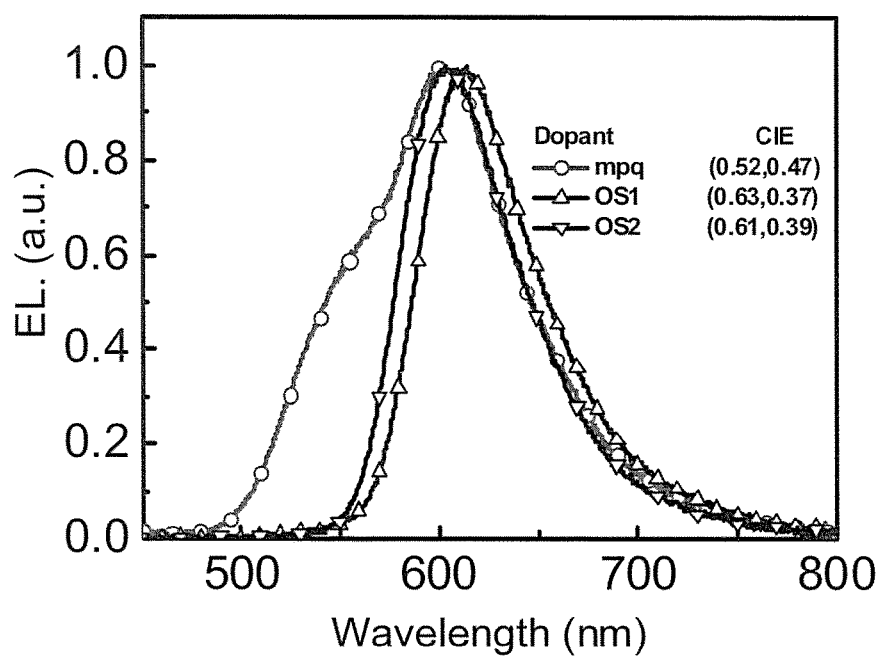
FIG. 19 is an EL spectra for the light emitting device of Examples 8-10.

FIG. 17 shows J-V-L characteristics of Examples 8-10. FIG. 18 shows EQE and PE as a function of brightness in accordance with Examples 8-10. FIG. 19 shows an EL spectra for the light emitting device of Examples 8-10. The pertinent data are summarized in Table 3.

TABLE 3

| Dopant | $V_{on}$ [V] | $L_{max}$ [cd/m²] | $I_{max}$ [mA/cm²] | $h_{ext}$ max [%, cd/A] | $h_p$ max [lm/W] | EQE at 1000 nit [%, V] |
|---|---|---|---|---|---|---|
| 1 wt % mpq | 4.0 | 75210 (14.8 V) | 3002.5 | 20.8, 49.5 | 32.4 | 16.7, 6.0 |
| 1 wt % OS1 | 3.6 | 161231 (15.0 V) | 3329.1 | 32.2, 48.1 | 32.4 | 31.1, 6.0 |
| 1 wt % OS2 | 3.6 | 189803 (16.2 V) | 933.3 | 35.0, 64.7 | 41.1 | 34.7, 6.0 |

As shown in FIGS. 17-19 and Table 3, all devices of examples 8-10 have high EQE up to 34.7% (35.0 cd/A, 41.1 lm/W) at a low driving voltage of 3.6 V at 1000 nit.

In summary, the triazine-based compound represented by formula (I), CN-T2T can function as an electron acceptor with an electron acceptor to form a highly efficient exciplex systems, or it may be used in an electron transport layer of a light emitting device. The light emitting device containing CN-T2T can have high EQE at low driving voltage. Moreover, by mixing or combining a blue-light emitting element, a white-light emitting device can be accomplished.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A triazine-based compound represented by formula (I):

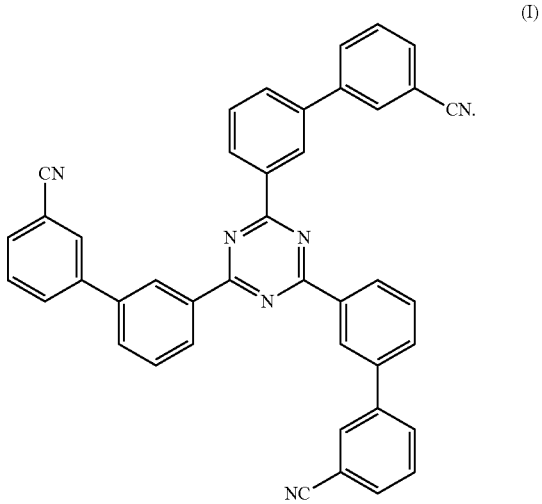 [SMILES: N#Cc1cccc(-c2cccc(-c3nc(-c4cccc(-c5cccc(C#N)c5)c4)nc(-c4cccc(-c5cccc(C#N)c5)c4)n3)c2)c1]

(I)

2. A light emitting device, comprising:
a cathode;
an anode;
an organic light emitting layer disposed between the anode and the cathode;
a hole transport layer disposed between the organic light emitting layer and the anode, and
an electron transport layer disposed between the organic light emitting layer and the cathode, wherein the electron transport layer comprises the triazine-based compound according to claim 1.

3. The light emitting device according to claim 2, wherein the electron transport layer further comprises a triazine-based compound represented by formula (II)

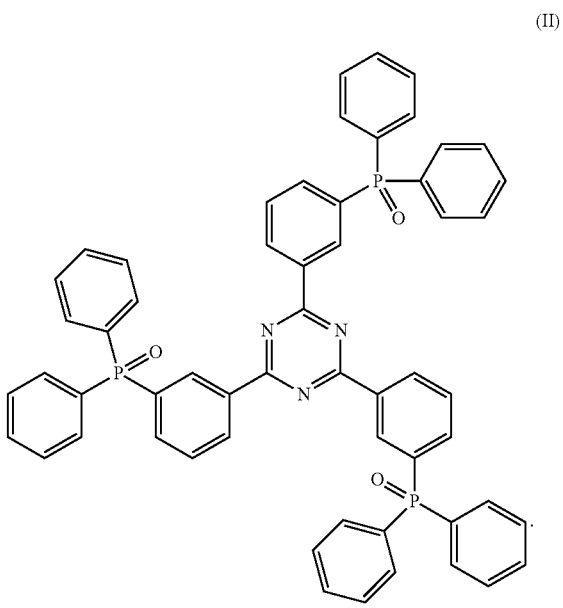 [SMILES: O=P(c1ccccc1)(c1ccccc1)c1cccc(-c2nc(-c3cccc(P(=O)(c4ccccc4)c4ccccc4)c3)nc(-c3cccc(P(=O)(c4ccccc4)c4ccccc4)c3)n2)c1]

(II)

4. A light emitting device, comprising:
a cathode;
an anode;
a hole transport layer disposed between the cathode and the anode; and
an organic layer disposed between the cathode and the hole transport layer, wherein the organic layer comprises the triazine-based compound according to claim 1 and an organic compound, a combination of the triazine-based compound and the organic compound forms an exciplex, a difference between a LUMO level of the triazine-based compound and a HOMO level of the organic compound is 2.92 eV or less.

5. The light emitting device according to claim 4, wherein an energy level offset between the HOMO levels of the triazine-based compound and the organic compound is more than 0.4 eV, and an energy level offset between the LUMO levels of the triazine-based compound and the organic compound is more than 0.4 eV.

6. The light emitting device according to claim 4, wherein the exciplex is used as an emitter.

7. The light emitting device according to claim 4, wherein the organic compound comprises caibazole derivative (Tris-PCz), 4,4',4"-tri(N-carbazolyl) triphenylamine (TCTA) or di-[4-(N,N-ditolyl-amino)-phenyl]cyclohexane (TAPC).

8. The light emitting device according to claim 4, wherein the organic layer further comprises a dopant, and the exciplex is used as a co-host.

9. The light emitting device according to claim 8, wherein the dopant has a singlet energy lower than that of the exciplex, and the dopant has a triplet energy lower than that of the exciplex.

10. The light emitting device according to claim 8, wherein the dopant comprises a fluorescent dopant or a phosphorescent dopant.

11. The light emitting device according to claim 10, wherein the fluorescent dopant comprises a red fluorescent dopant or a yellow fluorescent dopant.

12. The light emitting device according to claim 10, wherein the phosphorescent dopant comprises a red phosphorescent dopant or a yellow phosphorescent dopant.

13. A light emitting device, comprising:
a cathode;
an anode;
two light-emitting elements disposed between the cathode and the anode; and
a charge generation layer disposed between the two light-emitting elements, wherein each of the light-emitting elements comprises the triazine-based compound according to claim 1 and an organic compound with a red dopant, a combination of the triazine-based compound and the organic compound forms an exciplex for being a co-host, a difference between a LUMO level of the triazine-based compound and a HOMO level of the organic compound is 2.92 eV or less, the red dopant has a singlet energy lower than that of the exciplex, and the red dopant has a triplet energy lower than that of the exciplex.

14. The light emitting device according to claim 13, wherein the red dopant comprises a red fluorescent dopant or a red phosphorescent dopant.

15. The light emitting device according to claim 13, wherein the organic compound comprises di-[4-(N,N-ditolyl-amino)-phenyl]cyclohexane (TAPC).

16. A light emitting device, comprising:
a cathode;
an anode;
a green-light emitting element, a blue-light emitting element, and a red-light emitting element disposed between the anode and the cathode, wherein the green-light emitting element comprises the triazine-based compound according to claim 1 and an organic compound, and the red-light emitting element comprises the triazine-based compound according to claim 1 and the organic compound with a red dopant; and
a plurality of charge generation layers disposed between two of the green-light emitting element, the blue-light emitting element, and the red-light emitting element,
wherein a combination of the triazine-based compound and the organic compound forms an exciplex, a difference between a LUMO level of the triazine-based compound and a HOMO level of the organic compound is 2.92 eV or less, the red dopant has a singlet energy lower than that of the exciplex, and the red dopant has a triplet energy lower than that of the exciplex.

17. The light emitting device according to claim 16, wherein the red dopant comprises a red fluorescent dopant or a red phosphorescent dopant.

18. The light emitting device according to claim 16, wherein the organic compound comprises caibazole derivative (Tris-PCz), 4,4',4"-tri(N-carbazolyl)triphenylamine (TCTA) or di-[4-(N,N-ditolyl-amino)-phenyl]cyclohexane (TAPC).

* * * * *